(12) United States Patent
Mohammadi et al.

(10) Patent No.: US 10,851,042 B2
(45) Date of Patent: Dec. 1, 2020

(54) SOLUBIZATION OF RESVERATROL GLYCOLATE AND TARTRATE DERIVATIVES

(71) Applicant: ELC MANAGEMENT LLC, Melville, NY (US)

(72) Inventors: Fatemeh Mohammadi, Hauppauge, NY (US); Anna Czarnota, Commack, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 16/899,432

(22) Filed: Jun. 11, 2020

(65) Prior Publication Data

US 2020/0299223 A1    Sep. 24, 2020

Related U.S. Application Data

(63) Continuation-in-part of application No. 16/081,842, filed as application No. PCT/US2017/020923 on Mar. 6, 2017, now Pat. No. 10,717,698.

(60) Provisional application No. 62/304,541, filed on Mar. 7, 2016.

(51) Int. Cl.
*C07C 69/70* (2006.01)
*C07C 69/34* (2006.01)

(52) U.S. Cl.
CPC .............. *C07C 69/70* (2013.01); *C07C 69/34* (2013.01)

(58) Field of Classification Search
CPC .................................. C07C 69/70; C07C 69/34
See application file for complete search history.

(56) References Cited

U.S. PATENT DOCUMENTS

| 9,220,669 B2 | 12/2015 | Bratescu et al. |
| 2006/0173065 A1 | 8/2006 | Bezwada |
| 2008/0139650 A1 | 6/2008 | Jakob et al. |
| 2009/0215881 A1 | 8/2009 | Delaire et al. |
| 2017/0210694 A1 * | 7/2017 | Boo ........................ A61K 8/375 |

FOREIGN PATENT DOCUMENTS

| KR | 20050011174 | 1/2005 |
| KR | 20140094394 | 7/2014 |
| KR | 101735996 | 5/2017 |
| WO | WO-2009/017866 | 2/2009 |
| WO | WO-2009/023416 | 2/2009 |
| WO | WO-2009/032896 | 3/2009 |
| WO | WO-2013/008194 | 1/2013 |
| WO | WO-2016/011319 | 1/2016 |

OTHER PUBLICATIONS

Beutel, et al.; Resolution of Racemic [alpha]-Hydroxy-[beta]-[beta]-dimethyl-[gamma]- butyrolactone; Journal of the American Chemical Society; vol. 68; No. 8; pp. 1463-1465; Aug. 1946.
Kam, et al.; [(Arylcarbonyl)oxy]propanolamines. 1. Novel .beta.-Blockers with Ultrashort Duration of Action; Journal of Medicianl Chenmistry; vol. 27; No. 8; pp. 1007-1016; Aug. 1984.
Kim, et al.; Supporting Information—Multivalent Nanofibers of a Controlled Lenght: Regulation of Bacterial Cell Agglutination; Journal of the American Chemical Society; pp. S1-S16; Sep. 2012.
PCT International Search Report; International Application No. PCT/US2017/020923; Completion Date: Jun. 13, 2017; dated Jun. 13, 2017.
PCT Written Opinion of the International Searching Authority; International Application No. PCT/US2017/020923; Completion Date: Jun. 13, 2017; dated Jun. 13, 2017.
Supplementary European Search Report; EP Application No. 17763831.9; Completion Date: Jun. 19, 2019; dated Jul. 11, 2019.

* cited by examiner

*Primary Examiner* — Paul A Zucker
(74) *Attorney, Agent, or Firm* — Sonsy P. Rajan

(57) ABSTRACT

A process for solubilizing a resveratrol glycolate compound by heating the resveratrol glycolate and mixing the resveratrol glycolate with one or more glycols is disclosed. The process comprises an initial heating step of the resveratrol compound to a temperature not greater than 45° C. and a mixing step that mixes the heated resveratrol glycolate compound with at least one glycol solvent at room temperature for ten minutes to one hundred and twenty minutes.

7 Claims, 12 Drawing Sheets

SOLUBIZATION OF RESVERATROL GLYCOLATE AND TARTRATE DERIVATIVES

CROSS-REFERENCE TO RELATED APPLICATIONS

This application is a Continuation-In-Part of U.S. Non-Provisional patent application Ser. No. 16/081,842 filed Aug. 31, 2018, and granted as U.S. Pat. No. 10,717,698, which is a national stage application of International Application No. PCT/US17/20923 filed on Mar. 6, 2017, now expired, and which claims priority from U.S. Provisional Application No. 62/304,541 filed on Mar. 7, 2016, all of the applications are incorporated herein by reference in entirety.

FIELD

The invention is in the field of resveratrol derivative compounds and compositions, and methods for synthesizing same.

BACKGROUND

Resveratrol, also referred to as 3,5,4'-trihydroxystilbene, is a polyhydroxy-substituted compound having the general formula:

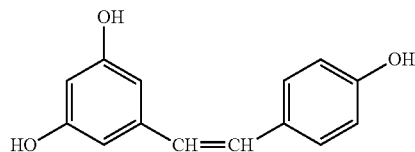

It is present in red grapes, raspberries, blueberries, and certain other plant berries or extracts. It is known that resveratrol is a potent anti-oxidant and has other anti-aging, anti-cancer, and antiviral effects. Because of its perceived fountain-of-youth properties, resveratrol has been incorporated into a variety of cosmetic formulations, such as skin creams. However, because resveratrol is somewhat unstable it readily discolors. In addition, it is most desirable to react resveratrol with other compounds to create resveratrol derivatives in order to maximize its effectiveness for properties such as stability, activity, and beneficial effects on skin.

Alpha hydroxy acids or AHA's are known for their effectiveness in treating skin. The carboxylic acid groups on the compounds aid in skin exfoliation to remove dead skin cells and debris from skin surfaces. It is also said that AHA's reduce the appearance of age-related skin changes such as lines, wrinkles, age spots, mottling, yellowing, and skin laxity. However, AHA's can also cause skin irritation, redness, or dryness in individuals with overly sensitive skin.

Particularly effective AHAs are glycolic and tartaric acids. Glycolic acid has the following formula:

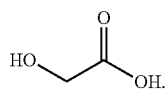

I

And tartaric acid the following formula:

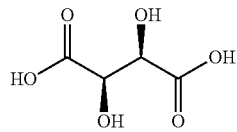

Esterifying resveratrol with glycolic or tartaric acids provides a resveratrol derivative that may be a mono-, di-, or tri-substituted ester on the hydroxyl group to form resveratrol mono-, di- or triglycolate or mixtures thereof, or resveratrol mono-, di-, or tritartrate or mixtures thereof, respectively. Such derivatives can be incorporated into cosmetic compositions to provide beneficial effects such as stimulating collagen or fibrillin synthesis, exfoliating skin, whitening skin, treating acne or other skin lesions, and inhibiting matrix metalloproteinases that degrade collagen.

SUMMARY

Embodiments herein are directed to a compound of the formula:

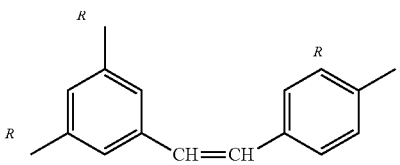

Wherein each R is independently selected from:
(i) —OH, or
(ii)

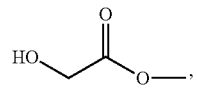

or
(iii)

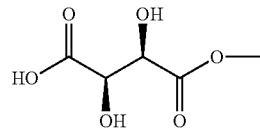

With the proviso that all three R cannot simultaneously be —OH.

The invention is also directed to a method for synthesizing an ester of resveratrol and glycolic acid by:
a) deprotonating resveratrol by reacting with a base,
b) preparing alpha hydroxyl protected glycolic acid by:
 (i) reacting the alpha hydroxyl group of glycolic acid with compound having a protecting donor group to form a protected alpha hydroxy glycolic acid
 (ii) reacting (i) with halogen donor compound to form a reactive alpha hydroxyl acyl halide,
c) reacting (a) and (b) to form alpha hydroxyl protected resveratrol glycolate; and
d) deprotecting the protected alpha hydroxyl groups to form resveratrol glycolate.

The invention is also directed to a method for synthesizing resveratrol tartrate comprising the steps of:
(a) deprotonating resveratrol by reacting with a base,
(b) preparing alpha hydroxyl protected tartaric acid anhydride by:
    (i) dehydrating tartaric acid to form a reactive tartaric acid anhydride,
    (ii) simultaneously reacting the alpha hydroxyl groups with a compound having a protecting donor group to form a protected tartaric acid anhydride,
(c) reacting (a) and (b) to form alpha hydroxyl protected resveratrol tartrate; and
(d) deprotecting the protected alpha hydroxyl groups to form resveratrol tartrate.

The invention is also directed to a topical composition comprising a compound of the formula:
Embodiments herein are also directed to a compound of the formula:

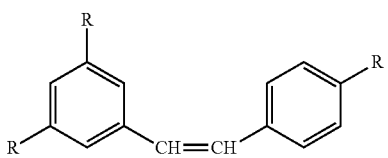

Wherein each R is independently selected from:
(i) —OH, or
(ii)

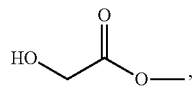

or
(iii)

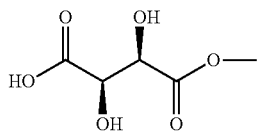

With the proviso that all three R cannot simultaneously be —OH.

The invention is also directed to a method or process of solubilizing a resveratrol glycolate by:
(a) heating the resveratrol glycolate compound and
(b) mixing the resveratrol glycolate compound with at least one glycol solvent at room temperature for about ten minutes to about one hundred and twenty minutes.

DETAILED DESCRIPTION

Figure 1:
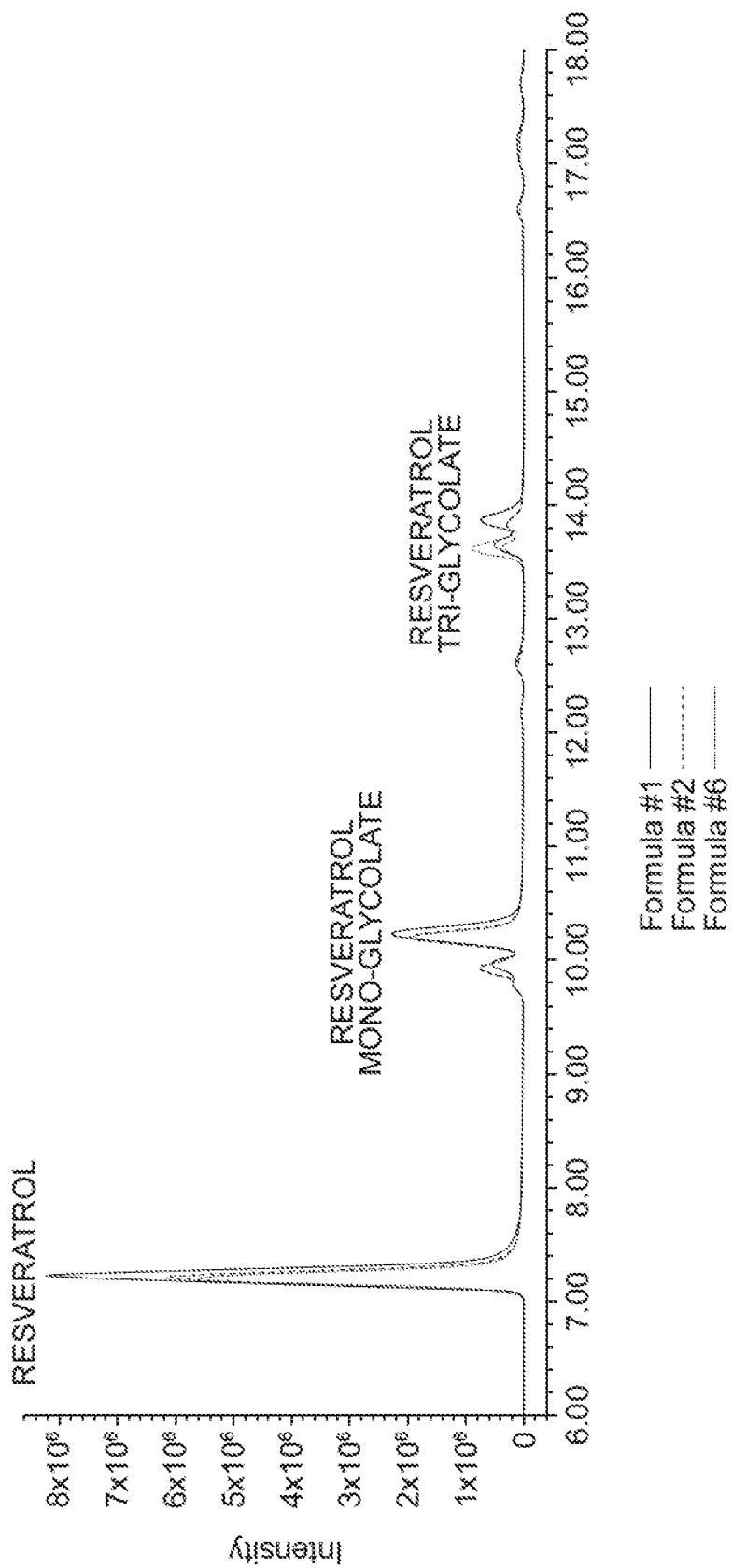
FIG. 1 shows the HPLC chromatogram of resveratrol glycolate (1%) at 4° C.

Resveratrol Glycolate
The ester of resveratrol and glycolic acid may be made as follows:
a) deprotonating resveratrol by reacting with a base,
b) preparing alpha hydroxyl protected glycolic acid by:
    (i) reacting the alpha hydroxyl group of glycolic acid with compound having a protecting donor group to form a protected alpha hydroxy glycolic acid
    (ii) reacting (i) with halogen donor compound to form a reactive alpha hydroxyl acyl halide,
c) reacting (a) and (b) to form alpha hydroxyl protected resveratrol glycolate; and
d) deprotecting the protected alpha hydroxyl groups to form resveratrol glycolate.

A suitable base for deprotonating resveratrol includes alkali or alkaline earth metal hydrides such as sodium, potassium, magnesium, lithium and so on. Preferably about 0.5 to 2 mole, most preferably 1 mole of resveratrol is reacted with from about 2 to 10 moles of metal hydride, preferably sodium hydride. In addition the reaction conditions are in the presence of anhydrous argon gas and tetrahydrofuran at room temperature (25° C.). The reaction conditions may range from 1 to 10 hours, most preferably 2 to 6 hours, and will yield deprotonated resveratrol where all three hydrogens are removed from the three hydroxyl groups of resveratrol.

Separately, glycolic acid is reacted with compound having a protecting donor group. Most preferred are pyran compounds which are heterocyclic non-aromatic rings, and in particular mono-, di-, tri-, or tetrahydropyrans (where the mono-, di-, tri- and tetra- refer to the number of hydrogen atoms removed from the pyran ring) and a short chain mono-, di-, or trialkyl halogen where the alkyl is a short chain alkyl such as methyl, ethyl, propyl, and the halogen is chlorine, fluorine, bromine, etc. Most preferred is dimethyl chloride. The reaction may take place in the presence of pyridine, p-Toluenesulfonic acid, and is preferably at room temperature for a period of time ranging from 3-12 hours. More preferred is where the compound having a protecting donor group is dihydropyran, and the alkyl halide is a dimethyl halogen, and in particular dimethyl chloride. About 1.5 moles of dihydropyran is reacted with 1 mole of glycolic acid to yield the alpha hydroxyl glycolate protected with tetrahydropyran. Thereafter the reaction is continued in the presence of SOCl$_2$, dimethyl formamide, and dimethyl chloride under reflux conditions for 4 to 6 hours to yield glycolic acyl chloride where the alpha hydroxyl group is protected with tetrahydropyran. The final step is deprotecting the protected alpha hydroxyl acyl.

Alternatively, after deprotonating the glycolic acid, the hydroxyl group may be protected by reacting with trityl halogens such as trityl chloride (triphenyl methyl chloride) where the alpha hydroxyl group is substituted with triphenyl methyl group. Thereafter the protected compound is reacted with SOCl$_2$, dimethyl formamide, and dimethylchloride under reflux conditions for about 4-6 hours to yield a compound with the trityl protected alpha hydroxyl chloride group. Then, the trityl protected acyl halide form of the compound is reacted with the deprotonated resveratrol to form resveratrol glycolate where the alpha hydroxyl groups on the glycolic acid remain protected with the trityl group. The trityl protecting groups are removed by reaction with one or more of trifluoroacetic acid, ethanediol, dimethylsulfide and dimethylchloride to form resveratrol glycolate.

Another alternative is to purchase a commercially available 2-hydroxy acetyl chloride and react with the deprotonated resveratrol to form resveratrol glycolate. This reaction takes place in the presence of one or more of triethylamine and tetrahydrofuran at room temperature from 12 to 72 hours. The end result is resveratrol glycolate. Depending on the reaction conditions used and the reactant concentrations the resveratrol glycolate may be mono-, di-, or trisubstituted with glycolic acid or in the form of mixtures of the mono-, di-, or trisubstituted esters. In this case the different compounds include 3-glycolate-5-4'-dihydroxystilbene; 5-glycolate-3,4' dihydroxystilbene; 4'-glycolate-3,5-dihydroxystilbene; 3,5-diglycolate-4'-hydroxystilbene; 3,4'-diglycolate-5-hydroxystilbene; 3,4'-diglycolate-5-hydroxystilbene; 4'5-diglycolate-3-hydroxystilbene; and 3,5,4'-triglycolate stilbene.

Resveratrol Tartrate

The tartrate ester of resveratrol may be synthesized by first deprotonating resveratrol as noted above in synthesis of resveratrol glycolate and under same reaction conditions. Separately, tartaric acid is reacted in the presence of acetic anhydride, acetic acid, or pyridine at room temperature for 12-48 hours to yield the acetyl protected tartaric anhydride, O,O'-diacetyl-L-tartaric anhydride. Alternatively, this compound can be purchased commercially.

Thereafter, 1 mole of the deprotonated resveratrol is reacted with 3 moles of the O,O'-diacetyl-L-tartaric anhydride to form the acetyl protected resveratrol tartrate. The protecting groups are removed by reacting with potassium carbonate (10 mole) and methanol at room temperature for 1-6 hours to yield resveratrol tartrate. Depending on the reaction conditions and the amount of reactants used, the resveratrol may be mono-, di-, or tri-substituted with tartaric acid or may be in the form of mixtures of the mono-, di-, and tri-substituted tartaric acid substituted resveratrol. In this case the different compounds include 3-tartrate-5-4'-dihydroxystilbene; 5-tartrate-3,4' dihydroxystilbene; 4'-tartrate-3,5-dihydroxystilbene; 3,5-ditartrate-4'-hydroxystilbene; 3,4'-ditartrate-5-hydroxy stilbene; 3,4'-ditartrate-5-hydroxystilbene; 4'5-ditartrate-3-hydroxystilbene; and 3,5,4'-tritartrate stilbene.

Cosmetic Compositions

The resveratrol esters may be incorporated into topical cosmetic compositions that may be in the form of creams, lotions, serums, solutions, dipsersions and the like. The compositions may be in the formula of emulsions—either water-in-oil or oil-in-water. Suitable emulsions contain from about 1 to 90% water and 10-90% of other ingredients including oil. Such additional ingredients include, but are not limited to the following.

Oils

Suitable oils include silicones, esters, vegetable oils, synthetic oils, including but not limited to those set forth herein. The oils may be volatile or nonvolatile, and are preferably in the form of a pourable liquid at room temperature. If present, the oils may range from about 0.5 to 85%, preferably from about 1-75%, more preferably from about 5-65% by weight of the total composition.

Cyclic and linear volatile silicones are available from various commercial sources including Dow Corning Corporation and General Electric. The Dow Corning linear volatile silicones are sold under the trade names Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

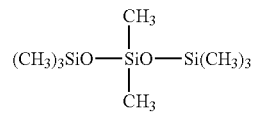

Methyl trimethicone purchased from, for example, Shin-Etsu Silicones under the trade name TMF-1.5, having a viscosity of 1.5 centistokes at 25° C.

Also suitable are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and C$_{8-20}$ isoparaffins. Suitable Cu isoparaffins are manufactured by Permethyl Corporation under the tradename Permethyl 99A. Various C$_{16}$ isoparaffins commercially available, such as isohexadecane (having the tradename Permethyl R), are also suitable.

Also suitable are esters formed by the reaction of a carboxylic acid and an alcohol. The alcohol and the carboxylic acids may both have fatty (C6-30) chains. Examples include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

The ester may also be in the dimer or trimer form. Examples of such esters include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Examples of other types of esters include those from arachidonic, citric, or behenic acids, such as triarachidin, tributyl citrate, triisostearyl citrate, tri C$_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone. Examples include dimethicone, phenyl dimethicone, diphenyl dimethicone, phenyl trimethicone, or trimethylsiloxyphenyl dimethicone. Other examples include alkyl dimethicones such as cetyl dimethicone, stearyl dimethcone, behenyl dimethicone, and the like.

Surfactants

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Silicone surfactants may be generically referred to as dimethicone copolyol or alkyl dimethicone copolyol. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers that contain at least one hydrophilic moiety such as polyoxyalkylenated groups. Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. All recitations of units include all whole integers between the range.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, thermus thermophilis ferment extract, camelina sativa seed oil, boswellia serrata extract, olive extract, *Aribodopsis Thaliana* extract, *Acacia Dealbata* extract, *Acer Saccharinum* (sugar maple), acidopholus, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officinalis, Citrus medica limonum, Panax ginseng, Siegesbeckia orientalis, Fructus mume, Ascophyllum nodosum*, Bifida Ferment lysate, *Glycine soja* extract, *Beta vulgaris, Haberlea rhodopensis, Polygonum cuspidatum, Citrus aurantium dulcis, Vitis vinifera, Selaginella tamariscina, Humulus lupulus, Citrus reticulata* Peel, *Punica granatum, Asparagopsis armata, Curcuma longa, Menyanthes trifoliata, Helianthus annuus, Hordeum vulgare, Cucumis sativus, Evernia prunastri, Evernia furfuracea*, and mixtures thereof.

Particulate Materials

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

The particulate matter may be colored or non-colored powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium tri silicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above-mentioned powders may be surface treated with lecithin, amino acids, mineral oil, silicone, or various other agents either alone or in combination, which coat the powder surface and render the particles more lipophilic in nature.

Suitable pigments are organic or inorganic. Organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

Vitamins and Antioxidants

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are retinyl palmitate, retinol. retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

The invention further comprises treating skin to stimulate collagen synthesis by topically applying a composition tri- or tetrapeptide, at least one penta- or hexapeptide, at least one extract from the *Laminaria* genus, and whey protein. The compositions may be applied in the forms mentioned herein, as part of skin care regimens. For example, the composition may be applied to the skin as a night cream or cream applied to skin prior to a period of bodily rest such as a nap or sleep. The composition may be applied two times a day, in the morning and in the evening after cleansing the skin. The composition may be applied to the skin over skin care products, in the form of foundations or other color cosmetics.

Solubility

Typically, the resveratrol glycolate as a raw material is a solid substance and is very difficult to formulate. In its original and raw material form, resveratrol glycolate is a rock-like solid substance with a hard texture and can be difficult to break apart for use in a formulation. Further, resveratrol glycolate can form clumps in a solution. Thus, resveratrol is difficult to solubilize or formulate, it is also very difficult to handle the raw material.

In the past, experiments have been performed to solubilize resveratrol glycolate in oils, alcohol or using emulsifiers. However, such solvents were unsuitable for cosmetic applications due to its harsh nature on the human skin and therefore, use of such solvents for cosmetic application was found unsuitable. Formulations intended for topical application on the human skin must be skin friendly. Also, such formulations should be easy to mix without clumping or forming cloudy mixtures. Further, in case of topical applications, products that comprise active ingredients in a solubilized form often exhibit increased availability on the skin than those products with dispersed active ingredients. Improved solubility of resveratrol glycolate improves ease of formulating the material. Further, when resveratrol glycolate is provided in solubilized form rather than in its original solid form, the pre-solubilized resveratrol glycolate can be added directly to a formula without further processing.

Given the difficulty to handle resveratrol in a solid form as well as the need for non-harsh and skin-friendly solvents, it is necessary to determine solvents that are capable of solubilizing resveratrol in a manner that is useful and adaptable for topical cosmetic applications. Various experiments were carried out to determine solubility of resveratrol glycolate, examples of which are shown below in Tables 1-4.

The present invention provides a method or process to solubilize resveratrol glycolate in an aqueous phase at a concentration of about 0.01% to about 30% to the total percentage of the solution. The process of solubilizing resveratrol glycolate according to the invention comprises the step of heating the resveratrol glycolate at a temperature not greater than 45° C. and the step of mixing the resveratrol glycolate with a glycol solvent at room temperature in propeller mixer for about ten (10) to about one hundred and twenty (120) minutes. In a preferred embodiment, the process of solubilizing resveratrol glycolate according to the invention comprises the step of heating the resveratrol glycolate at a temperature not greater than 45° C. and the step of mixing the resveratrol glycolate with a glycol cosolvent at room temperature in propeller mixer for about ten (10) to about one hundred and twenty (120) minutes. In a preferred embodiment, the starting raw material is warmed to about 40° C. prior to mixing. The length of time for solubilization (i.e., time for the resveratrol glycolate to dissolve and for the solution to turn clear) and appearance of the solution ranges from about 1 minute to about 120 minutes.

Surprisingly, the applicants effectively demonstrated that glycol solvents, particularly, the combination of at least two glycols cosolvents increases the solubility of resveratrol glycolate ire an aqueous phase. Among the glycol solvents, the exemplary are, butylene glycol, pentylene glycol, isoprene glycol, propanediol, butylene glycol, phenoxyethanol, ethoxydiglycol, butoxydiglycol, propylene glycol caprylate, polyethylene glycols (PEGS), and mixtures or combinations thereof. In a preferred embodiment, the glycol cosolvent employed is butylene glycol. In another preferred embodiment, the cosolvents employed in combination are pentylene glycol and butylene glycol. The ratio of cosolvents according to the invention is about 1:1 to about 1:100. In a preferred embodiment, pentylene glycol and butylene glycol are utilized in a ratio of about 1:5 to about 1:50. It must also be noted that resveratrol glycolate has limited solubility in glycerin.

The resulting resveratrol glycolate solution having solubilized resveratrol glycolate can be added directly into a formulation/composition at the appropriate temperature, or it can be used as a sub-phase for incorporating other ingredients (e.g., botanicals, particulates, and active materials listed above). Exemplary compositions include topical cosmetic compositions that may be in the form of creams, lotions, serums, solutions, dispersions and the like. The compositions may be in the form of emulsions, such as water-in-oil or oil-in-water emulsions.

Moreover, effectiveness of the resveratrol glycolate remains the same and is not negatively impacted when provided in solution or when formulated into a suitable form.

Resveratrol glycolate solution is stable at 4° C. for at about one to two years and at 50° C. for up to one month. In cosmetic applications, stability at 50° C. is considered to the harshest condition and therefore, a favorable stability at 50° C. generally translates to about two or three years of shelf life for the product according to the skilled in the art.

The invention will be further described in connection with the following examples which are set forth for the purposes of illustration only.

Example 1

Glycolic acid esters of resveratrol are prepared by reacting resveratrol (1 molar concentration) with NaH (6 molar) in a flow of argon gas in the presence of tetrahydrofuran, an aprotic solvent, at room temperature (25° C.) for 2-6 hours to form deprotonated resveratrol.

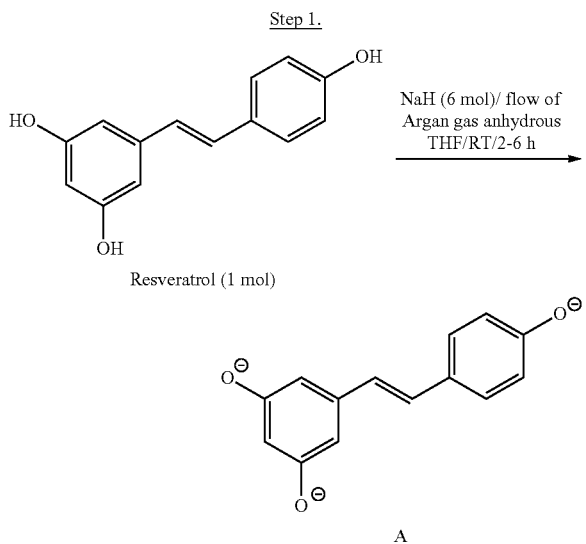

Then, glycolic acid is reacted with a mixture of dihydropyran (1.5 molar), p-Toluenesulfonic acid, pyridine, dimethylchloride, OC-RT for 3 to 12 hours to form glycolic acid where the terminal hydroxyl group has been protected with tetrahydropyran. The protected glycol acid is then reacted with a mixture of SOCl$_2$ (5 molar), dimethylformamide (cat.) and dimethylchloride under reflux conditions for 4-6 hours to form tetrahydropyran protected glycolic acyl chloride.

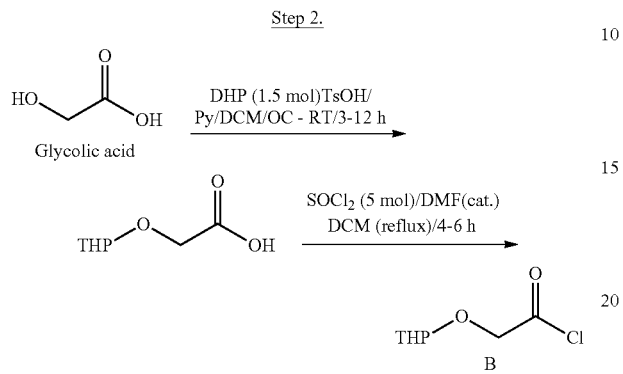

The deprotonated resveratrol formed in step (A) is then reacted with the protected glycolic acyl chloride (B) to form intermediate alpha hydroxyl protected resveratrol glycolate, which is then deprotected by reacting with mild acid to form resveratrol glycolate which is in the form of a mixture of mono-, di-, and triester forms.

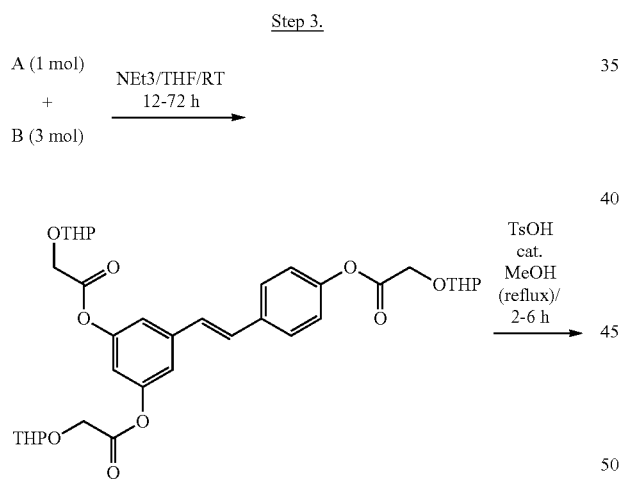

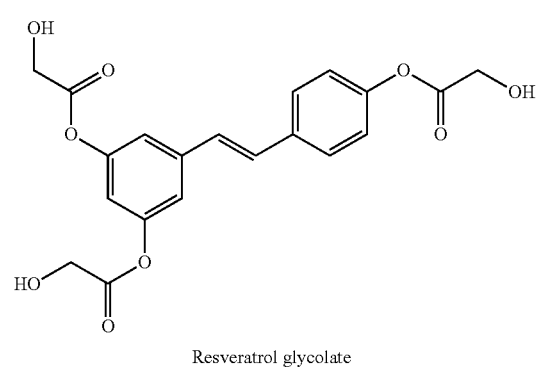

Resveratrol glycolate

-continued

NaH: Sodium hydide
DHP: Dihydropyran
DMF: Dimethyl formamide
DCM: Dimethychloride
TsOH: p-Toluenesulfonic acid
Trt: Trityl chloride
DIEA: N,N-Diisopropylethylamine
THF: Tertahydrofuran
TFA: Trifluoroacetic acid
EDT: 1,2-Ethanedithiol
MeOH: Methanol
NEt$_3$: Triethylamine Example 2

Resveratrol glycolate is prepared by deprotonating resveratrol in the same manner as Step 1 (A), above. Separately, glycolic acid is reacted with trityl chloride (1.5 molar) in N,N,-diisopropylethylamine (DIEA) to form glycolic acid where the hydroxyl group is protected with trityl chloride. The trityl chloride protected glycolic acid is then further reacted with SOCl$_2$ (5 molar), dimethylformamide (DMF), dimethylchloride (DMC) in reflux conditions for 4-6 hours to form trityl chloride protected glycolic acyl chloride.

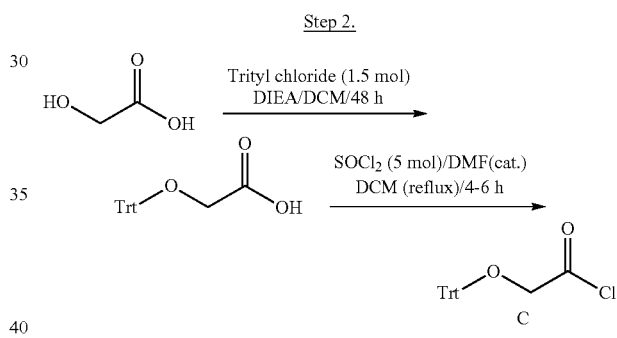

Then, 1 mole of (A) is mixed with 3 moles of (C) and reacted with triethylamine, tetrahydrofuran, at room temperature (25° C.) for 12-72 hours to form trityl chloride protected resveratrol glycolate which is thereafter treated with trifluoroacetic acid, 1,2-ethanediol, dimethylslfide and dimethylchloride to remove the protecting groups to yield resveratrol glycolate.

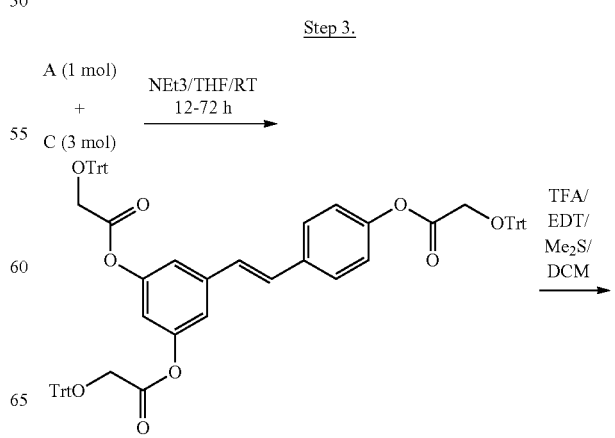

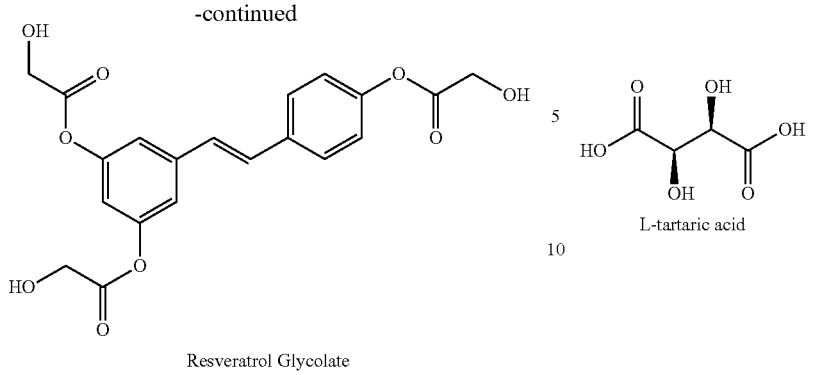

Resveratrol Glycolate

Example 3

Resveratrol glycolate is prepared by reacting the deprotonated resveratrol obtained in Step 1 (A) in Example 1 with a commercially available glycolic acyl chloride in the presents of triethylamine and tetrahydrofuran at room temperature for 12-72 hours to form resveratrol glycolate.

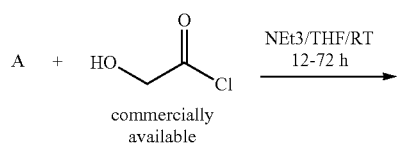

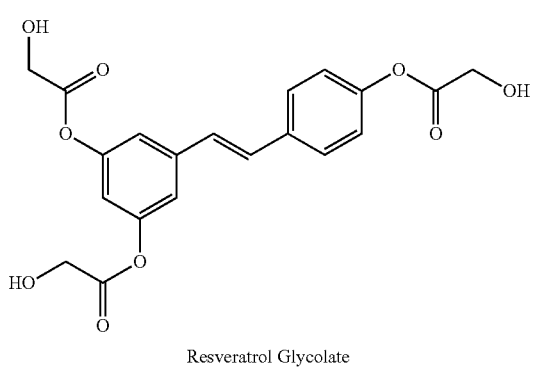

Resveratrol Glycolate

Example 4

Tartaric acid esters of resveratrol are prepared by deprotonating resveratrol in the same manner as set forth in Example 1, Step 1 (A). Then L-tartaric acid is reacted with a mixture of acetic acid, acetic anhydride and pyridine at room temperature for 12-48 hours to form +—O—O'-Diacetyl-L-tartaric anhydride.

Step 2.

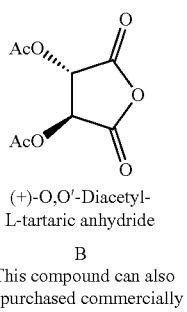

L-tartaric acid (+)-O,O'-Diacetyl-L-tartaric anhydride

B
(This compound can also be purchased commercially)

Then 1 mole of A is reacted with 3 moles of B in the presence of trimethylamine and tetrahydrofuran at room temperature for 12-72 hours to form acyl protected tartaric acid which si then reacted with $K_2CO_3$ (10 molar), methanol, OC-RT for 1 to hours to form resveratrol tartrate.

Step 3.

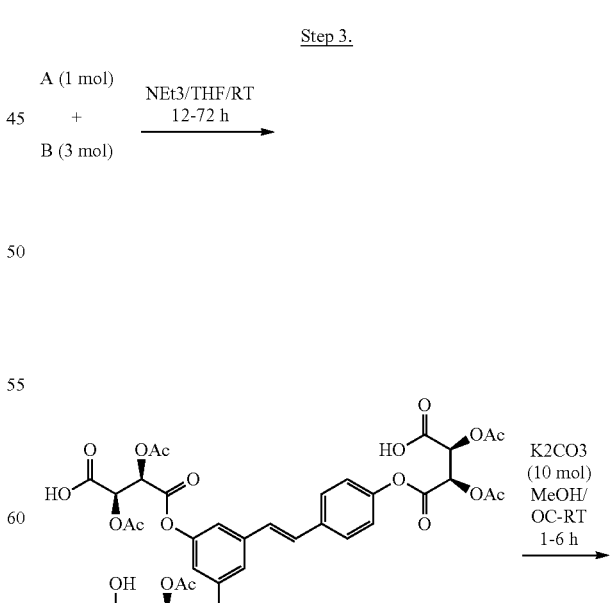

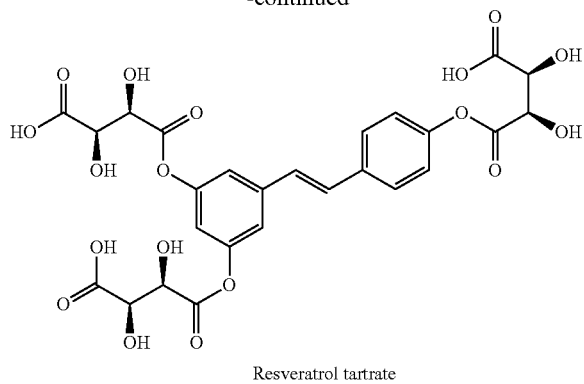

Resveratrol tartrate

The term "OC-RT" means zero degrees centigrade—room temperature.

Example 5

Emulsion compositions containing the resveratrol glycolate and tartrate are made as follows:

| Ingredient | #1 (Wt %) | #2 (Wt %) |
|---|---|---|
| Water | QS100 | QS100 |
| Resveratrol glycolate | 1.0 | — |
| Resveratrol tartrate | — | 0.5 |
| Glycerin | 10 | 10 |
| EDTA | 0.1 | 0.1 |
| PEG-60 hydrogenated castor oil | 0.1 | 0.1 |
| Phenoxyethanol | 0.5 | 0.5 |
| Carbopol | 0.3 | 0.5 |
| Behenyl alcohol | 0.5 | 0.5 |
| Glyceryl stearate SE | 4 | 8 |
| Tricaprylyl citrate | 5 | 5 |

The composition is prepared by combining the ingredients and mixing well to emulsify to a lotion.

Example 6

Anhydrous compositions are prepared as follows:

| Ingredient | #1 (Wt %) | #2 (Wt %) |
|---|---|---|
| Dimethicone/vinyl dimethicone crosspolymer/methyl trimethicone (10:90) | QS100 | QS100 |
| Resveratrol glycolate | 0.75 | — |
| Resveratrol tartrate | — | 2.0 |
| N-acetyl glucosamine | 0.5 | 0.5 |
| PEG-60 hydrogenated castor oil | 0.5 | 0.5 |
| Simmondsia chinensis (jojoba) seed oil | 20 | 20 |
| Glycerin | 10 | 10 |

The compositions are prepared by combining the ingredients and mixing well to form a serum.

Example 7: Solubility of Resveratrol Glycolate

Below experiments were performed to determine solubility of resveratrol glycolate in glycol solvents. As described in the present invention, glycols or glycol cosolvents improve the solubility of resveratrol glycolate. In addition, heating resveratrol glycolate raw material or the mixture can also improve the solubility of resveratrol glycolate. Heating step may be performed at a temperature not greater than 45° C. Each of the formulas in Table 1 were prepared by heating resveratrol glycolate sample to about 40° C. followed by mixing the heated resveratrol glycolate with the respective glycol solvent at room temperature using a propeller mixer for ten (10) to one hundred and twenty (120) minutes. The length of time to solubilize (i.e., for the resveratrol glycolate to dissolve and the solution to turn clear) and appearance of the solution was recorded.

As shown in Table 1, formula 2, resveratrol glycolate has relatively low solubility in glycerin. Table 2 shows examples of solubilizing various amounts of resveratrol glycolate in propanediol.

TABLE 1

| | | Resveratrol Glycolate Solubility in Glycol solvent: | | | |
|---|---|---|---|---|---|
| SEQ | Ingredient | Formula 1 (wt %) | Formula 2 (wt %) | Formula 3 (wt %) | Formula 4 (wt %) |
| 1 | Resveratrol glycolate | 1.00 | 1.00 | 1.00 | 1.00 |
| 2 | Glycerin | | 99.00 | | |
| 3 | Propanediol | 99.00 | | | |
| 4 | Butylene glycol | | | 99.00 | |
| 5 | Pentylene glycol | | | | 99.00 |
| | Observations: | after 10-15 mins of mixing, no visible solid particles, clear solution | after 1 hour of mixing, partially dissolved with visible particles | after 20-30 mins of mixing, no visible solid particles, clear solution | after 20 mins of mixing, no visible solid particles, clear solution |

Table 2 shows examples of solubilizing various amounts of resveratrol glycolate in propanediol. The formula in Table 2 were also prepared as described above by heating and mixing the respective amounts of resveratrol glycolate with propanediol at room temperature using a propeller mixer for ten (10) to one hundred and twenty (120) minutes. The length of time to solubilize (i.e., for the resveratrol glycolate to dissolve and the solution to turn clear) and appearance of the solution was recorded.

TABLE 2

Resveratrol Glycolate Solubility in Propanediol

| SEQ | Ingredient | Formula 6 (wt %) | Formula 7 (wt %) | Formula 8 (wt %) | Formula 9 (wt %) |
|---|---|---|---|---|---|
| 1 | Resveratrol glycolate | 10 | 15 | 20 | 25 |
| 2 | Propanediol | 90 | 85 | 80 | 75 |
|  | Observations: | after 20 mins of mixing, no visible solid particles, clear solution - yellowish orange | No visible particles are observed after mixing and heating up to 40 C., clear dark | No visible particles are observed after mixing and heating up to 40 C., clear dark | No visible particles are observed after mixing and heating up to 40 C., solution is clear but color is intense reddish brown |

As shown above in Table 1 and Table 2, propanediol can solubilize up to 25% resveratrol glycolate with propeller mixing at room temperature. Combinations of glycols and/or heating can also increase the solubility of resveratrol glycolate, thereby, improving the ease of formulating resveratrol glycolate.

Tables 3-5 shows the results of solubilizing resveratrol glycolate using a combination of glycol cosolvents. Samples were stored in 4° C. for 3 months, 50° C. for one month, following which they were removed and stored in ambient conditions until the experimental analysis that is described below. Table 3 below indicates the representative formulas and the related description along with the storage temperature.

TABLE 3

| Sample Identification | Sample Description |
|---|---|
| Formula 1 (4° C., 50° C.) | 1% of Res Glycolate in combination of Hydrolyte (pentylene glycol) + Butylene Glycol |
| Formula 2 (4° C., 50° C.) | 1% of Res Glycolate in combination of Zemea (propanediol) + Butylene Glycol |
| Formula 3 (4° C., 50° C.) | 10% of Res Glycolate in combination of Hydrolyte (pentylene glycol) + Butylene Glycol |
| Formula 4 (4° C., 50° C.) | 20% of Res Glycolate in combination of Hydrolyte (pentylene glycol)) + Butylene Glycol |
| Formula 6 (4° C., 50° C.) | 1% of Res Glycolate in Isoprene Glycol |
| Formula 7 (4° C., 50° C.) | 10% Res Glycolate in Isoprene Glycol |
| Formula 8 (4° C., 50° C.) | 1% of Res Glycolate in combination of Phenoxy Ethanol + Butylene Glycol |
| Formula 9 (4° C., 50° C.) | 30% of Res Glycolate in combination of Hydrolyte (pentylene glycol) + Butylene Glycol |

TABLE 4

Resveratrol Glycolate Solubility in Glycol Cosolvents:

| Ingredient | Formula 6 (wt %) | Formula 1 (wt %) | Formula 8 (wt %) | Formula 2 (wt %) | Formula 3 (wt %) | Formula 4 (wt %) | Formula 9 (wt %) |
|---|---|---|---|---|---|---|---|
| Resveratrol glycolate | 1.00 | 1.00 | 1.00 | 1.00 | 10 | 20 | 30 |
| Butylene glycol |  | 89.00 | 96.00 | 89.00 | 80 | 60 | 40 |
| Isoprene glycol | 99.0 |  |  |  |  |  |  |
| Pentylene glycol |  | 10.00 |  |  | 10 | 20 | 30 |
| Phenoxyethanol |  |  | 3.00 |  |  |  |  |
| Zemea (propanediol) |  |  |  | 10.00 |  |  |  |
| Observations: Immediate | no visible solid particles, clear solution | no visible solid particles, clear solution | no visible solid particles, clear solution | no visible solid particles, clear solution | no visible solid particles, clear solution | no visible solid particles, clear solution | no visible solid particles, clear solution |

TABLE 4-continued

Resveratrol Glycolate Solubility in Glycol Cosolvents:

| Ingredient | Formula 6 (wt %) | Formula 1 (wt %) | Formula 8 (wt %) | Formula 2 (wt %) | Formula 3 (wt %) | Formula 4 (wt %) | Formula 9 (wt %) |
| --- | --- | --- | --- | --- | --- | --- | --- |
| Observations: After Stability testing 4 weeks in 4 C. | Clear, sl yellow tone no precipitation | Clear, v.sl yellow tone, no precipitation | Clear, sl yellow tone, no precipitation | Clear, sl yellow color, no precipitation | Clear, sl brownish/ gold color no precipitation | Clear, light amber like color, no precipitation | Clear, orange-dark, no precipitation |
| Observations: After Stability testing 4 weeks in 50 C. | Discoloration - dark orange/amber color | Discoloration - dark orange like color | Discoloration - orange/yellow color | Discoloration - orange amber like color | Discoloration- intense amber like color | Discoloration - intense dark amber like color | Discoloration - intense dark color |

Table 4 shows the solubilization of resveratrol glycolate in formulas corresponding to Table 3. In further experiments, 1% of formulas 1-4, 6, 8 and 9 were introduced into water to determine whether any precipitation of resveratrol glycolate would occur in the aqueous phase. Stability of each of the formulas were also tested at 4° C. and 50° C. to determine if there any crystallization, precipitation or discoloration in low and elevated temperatures (4° C. and 50° C.) would occur. As observed in the Table 4, no visible solid particle was observed immediately following the analysis. After 4 weeks in 4° C., no precipitation was observed, and a clear solution was obtained. Stability experiments are described in the Example 8 below.

Example 8: Stability of Resveratrol Glycolate in Glycol Cosolvents

Figure 8:
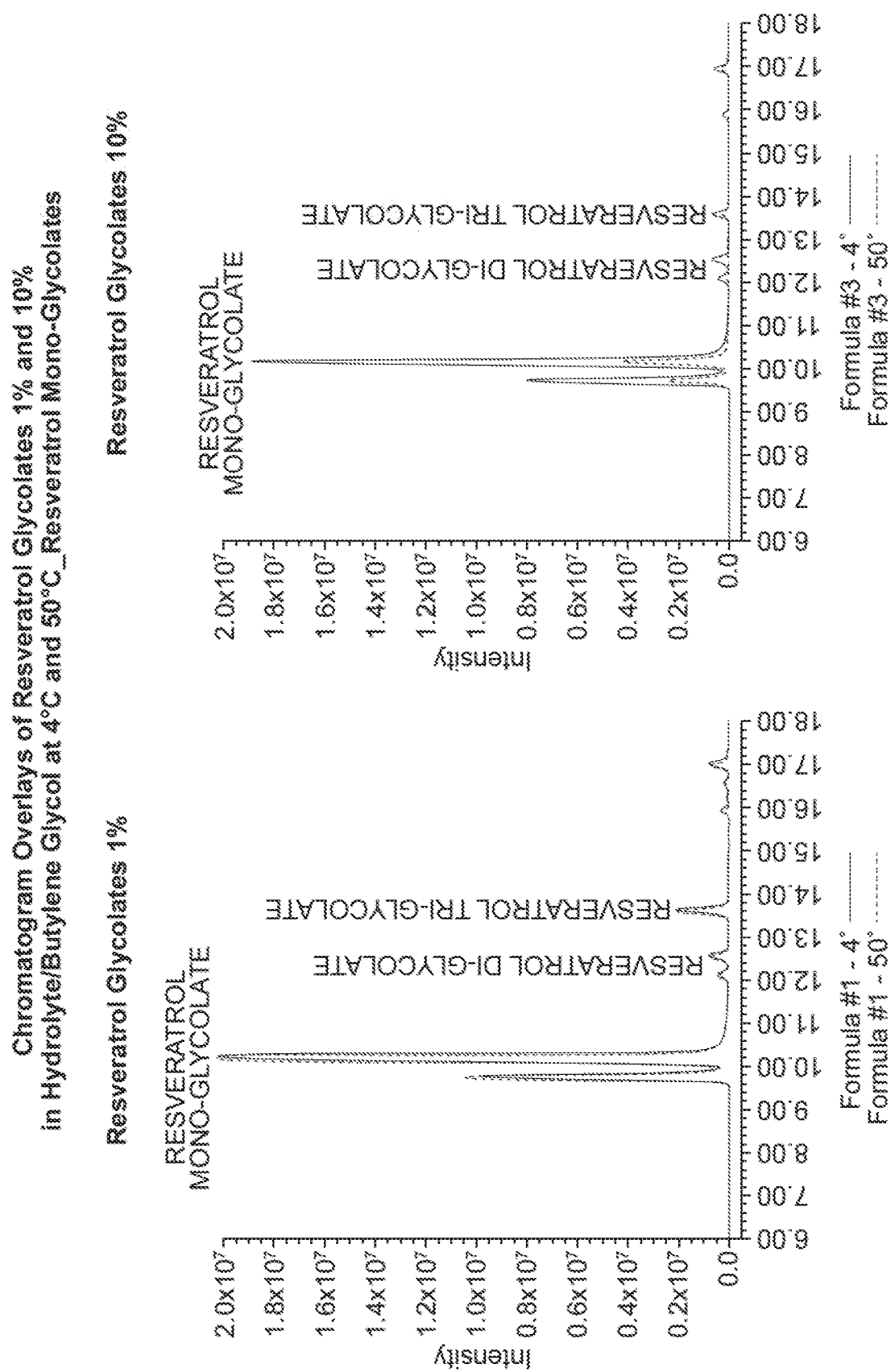
FIG. 8 shows the HPLC chromatogram of resveratrol mono glycolate in pentylene glycol and butylene glycol at 4° C. and 50° C., respectively.
Figure 9:
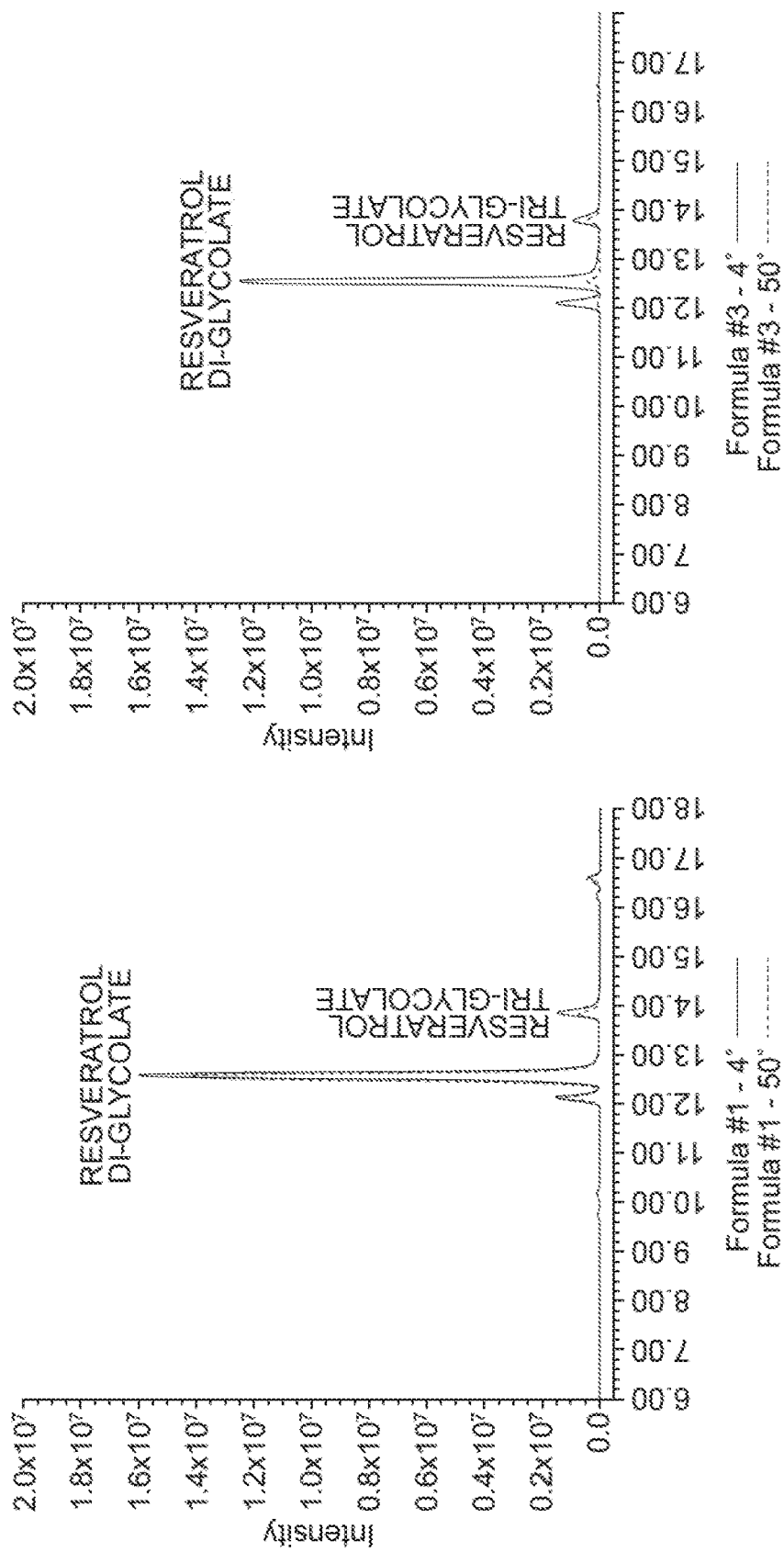
FIG. 9 shows the HPLC chromatogram of resveratrol di glycolate in pentylene glycol and butylene glycol at 4° C. and 50° C., respectively.
Figure 10:
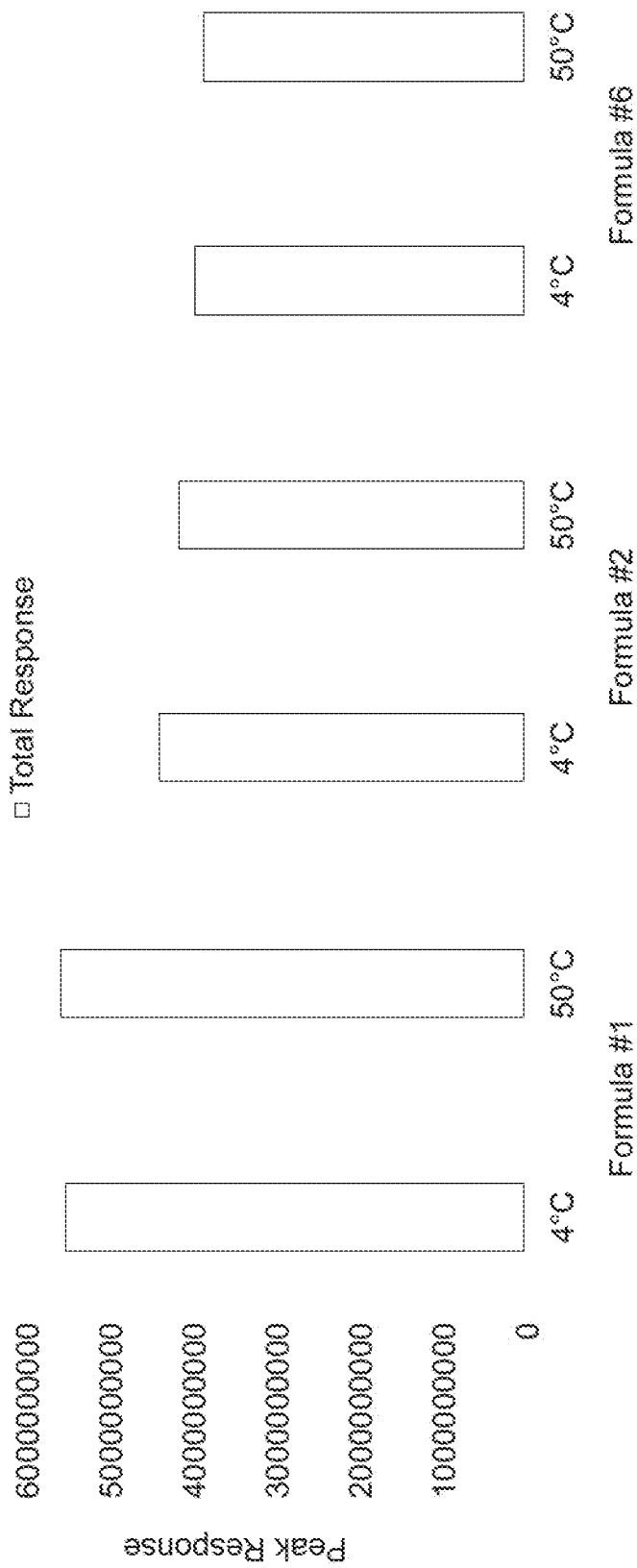
FIG. 10 shows stability of resveratrol glycolate (1%) in solution in respective formulas at 4° C. and 50° C.
Figure 11:
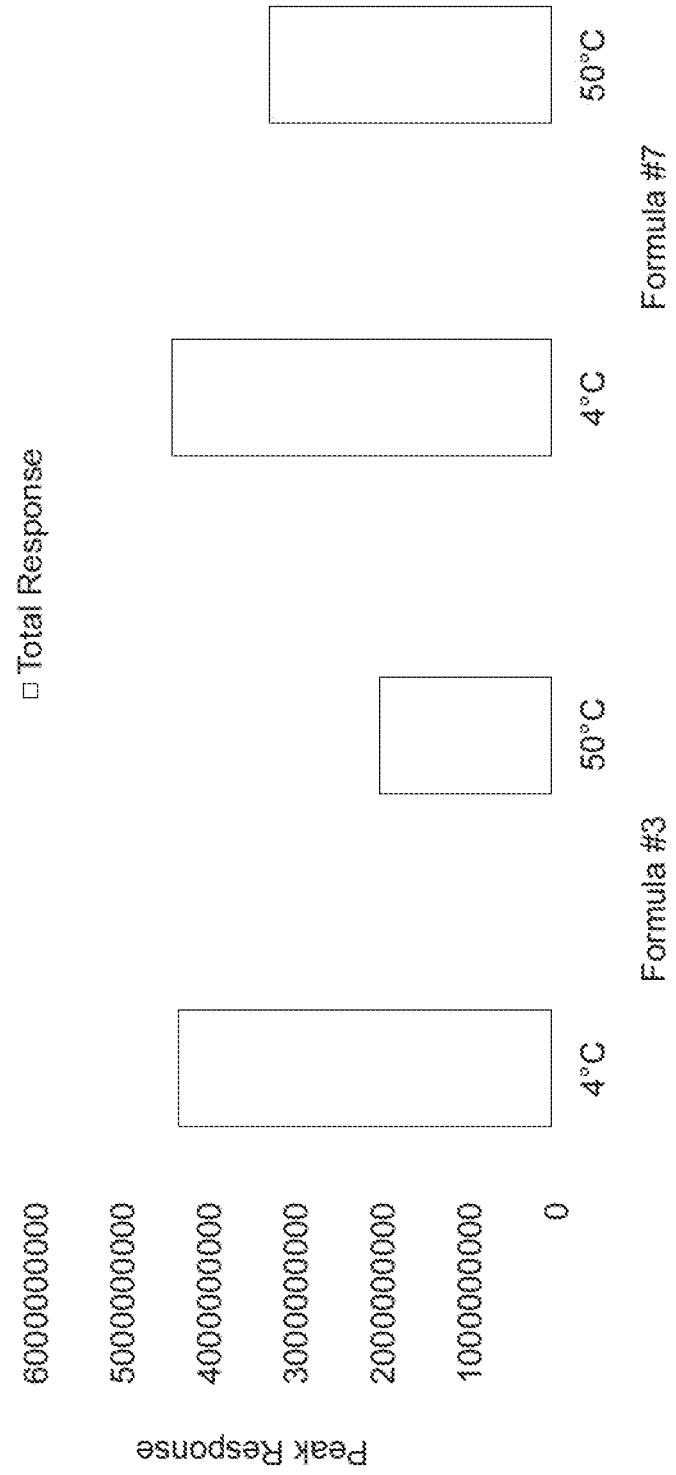
FIG. 11 shows stability of resveratrol mono and di glycolate (10%) in solution in respective formulas at 4° C. and 50° C.
Figure 12:
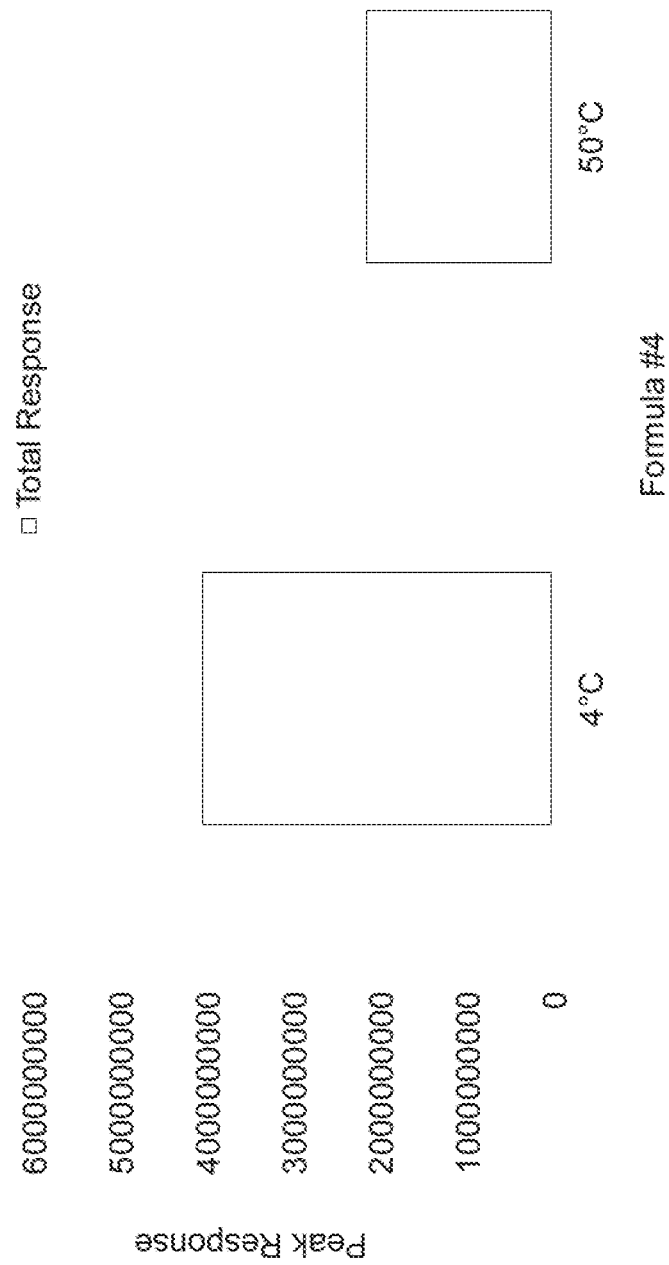
FIG. 12 shows stability of resveratrol mono and diglycolate (20%) in solution in respective formulas at 4° C. and 50° C.

In addition to determining solubility of resveratrol glycolate in glycol solvents, stability and amount of resveratrol glycolate (mono and di glycolate) in the samples were also determined. Experiments were performed using HPLC and the results were analyzed via LC-MS. Stability data obtained by HPLC chromatograms as shown in FIGS. 1-9. Results of HPLC chromatograms for resveratrol mono and di glycolate is shown in FIGS. 10-12.

Figure 2:
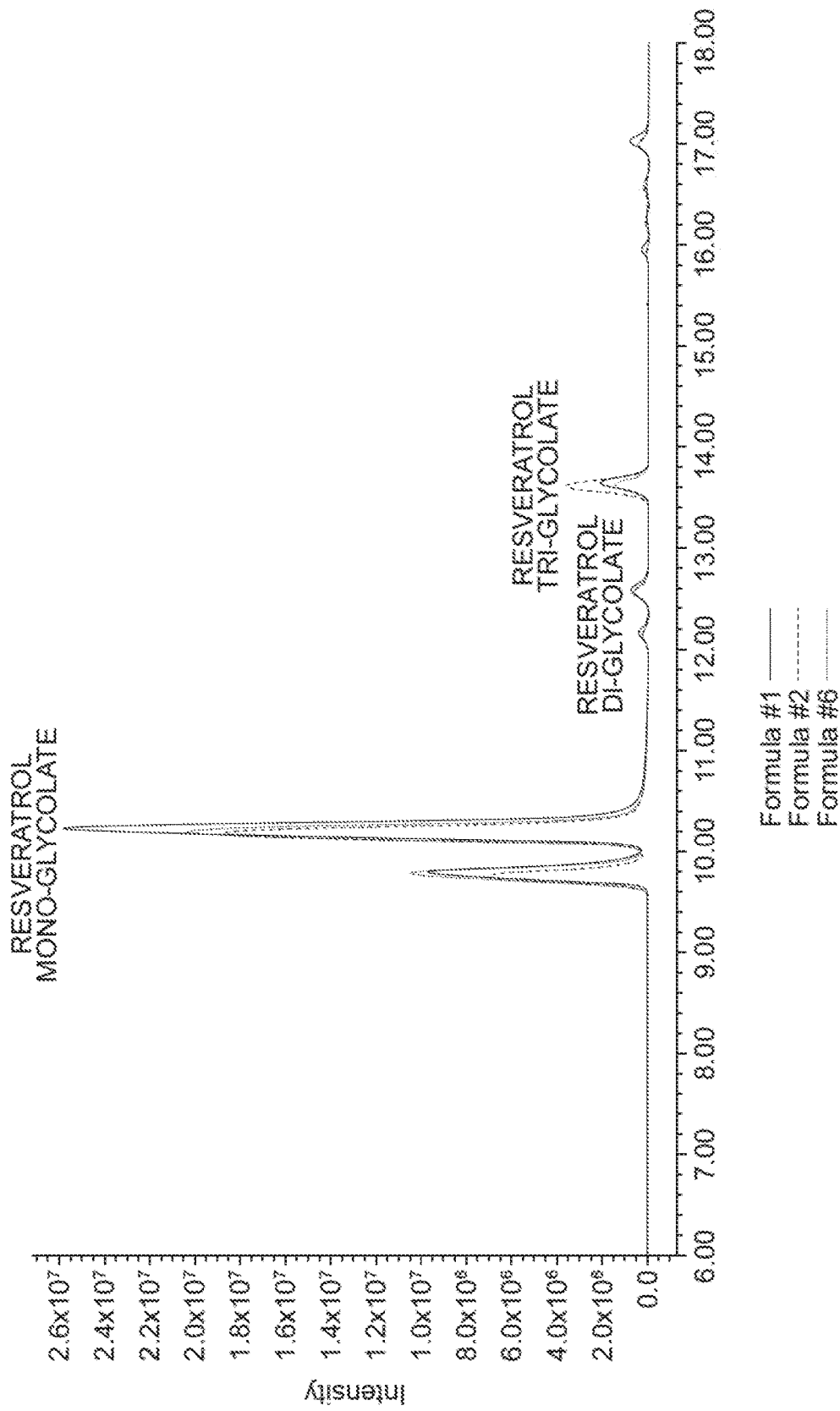
FIG. 2 shows the HPLC chromatogram of resveratrol mono glycolate (1%) at 4° C.
Figure 3:
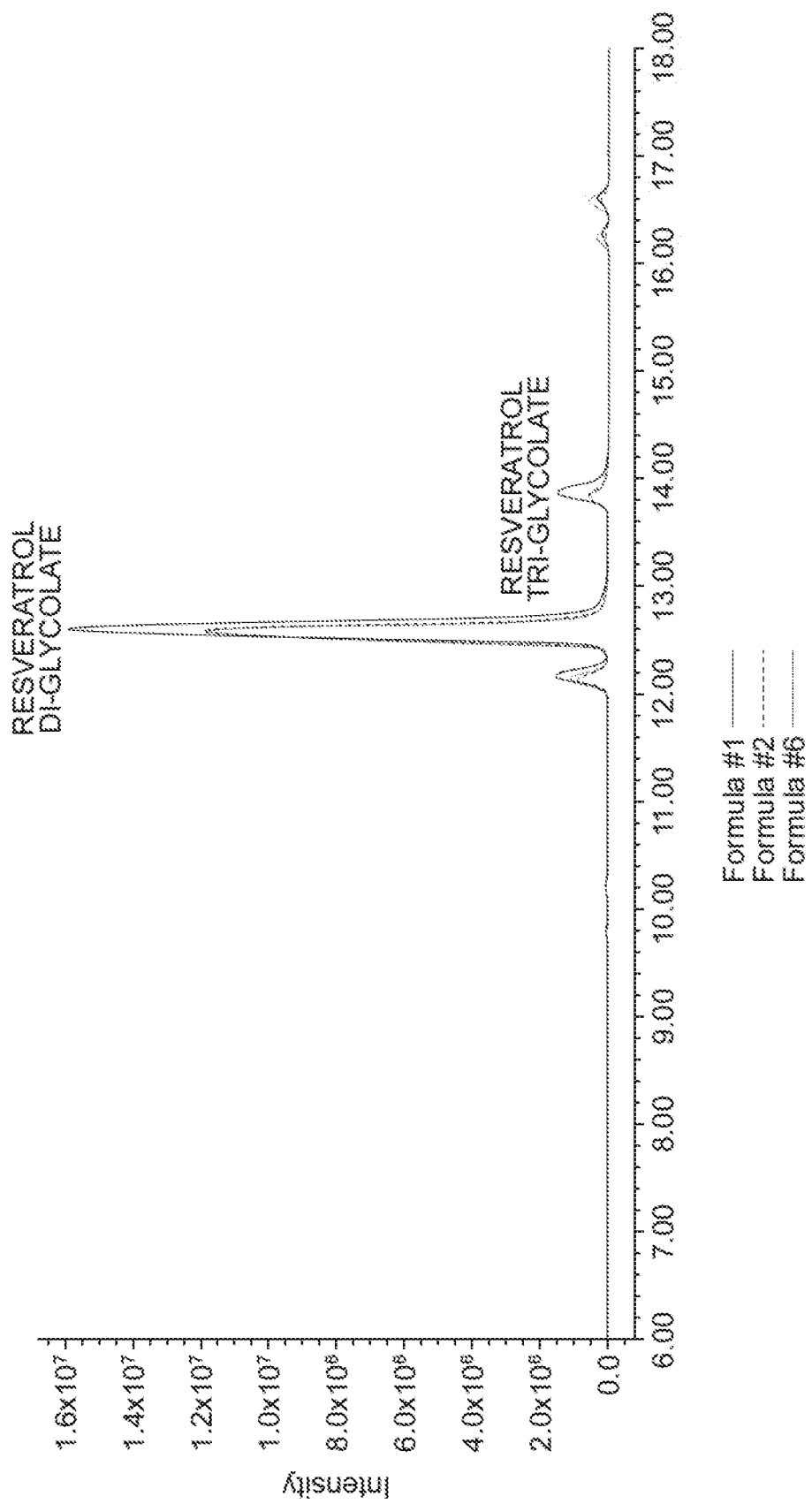
FIG. 3 shows the HPLC chromatogram of resveratrol di glycolate (1%) at 4° C.

FIG. 1 shows the HPLC chromatogram of resveratrol glycolate (1%) at 4° C. FIG. 2 shows the HPLC chromatogram of resveratrol mono glycolate (1%) at 4° C. FIG. 3 shows the HPLC chromatogram of resveratrol di glycolate (1%) at 4° C.

Figure 4:
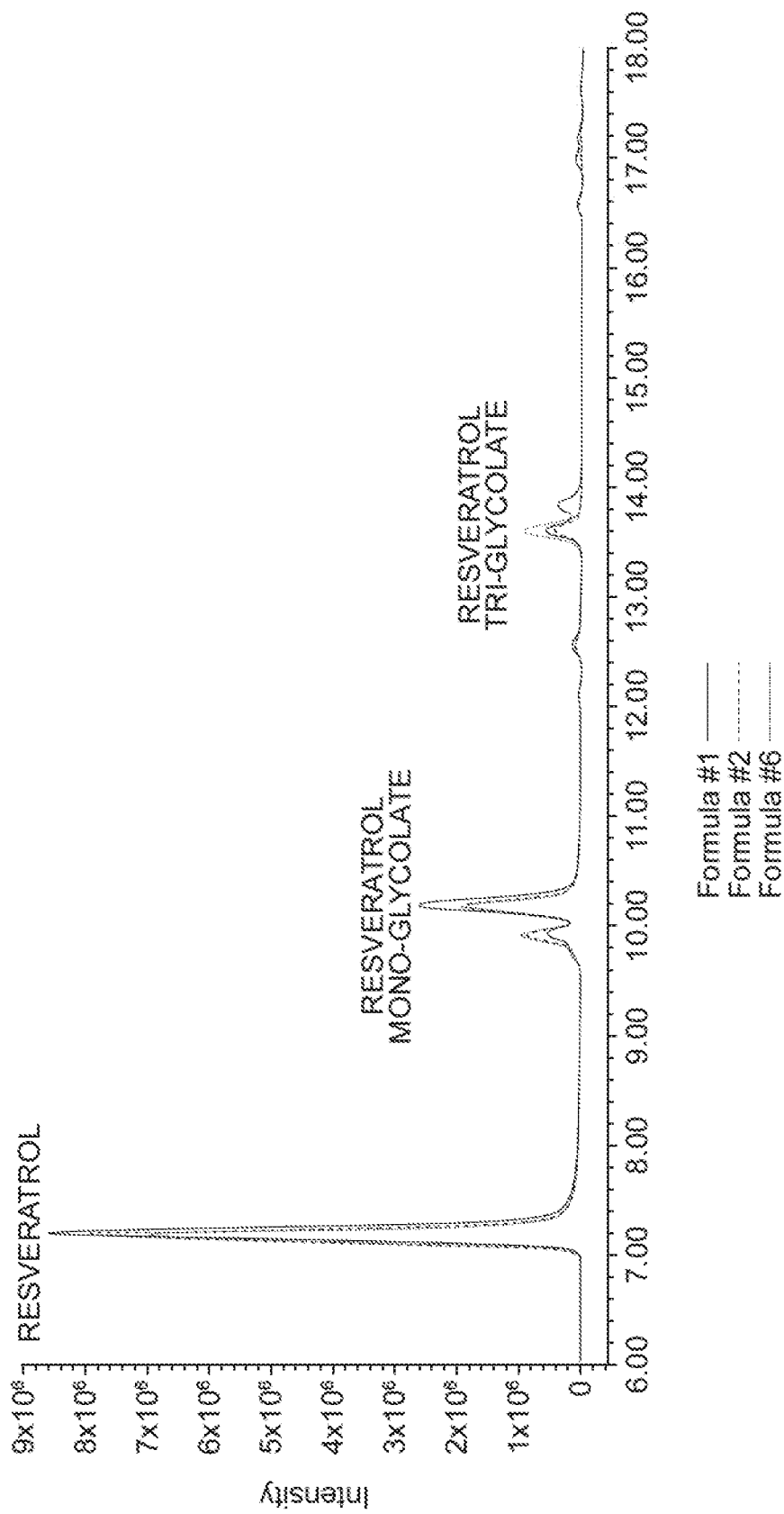
FIG. 4 shows the HPLC chromatogram of resveratrol glycolate (1%) at 50° C.
Figure 5:
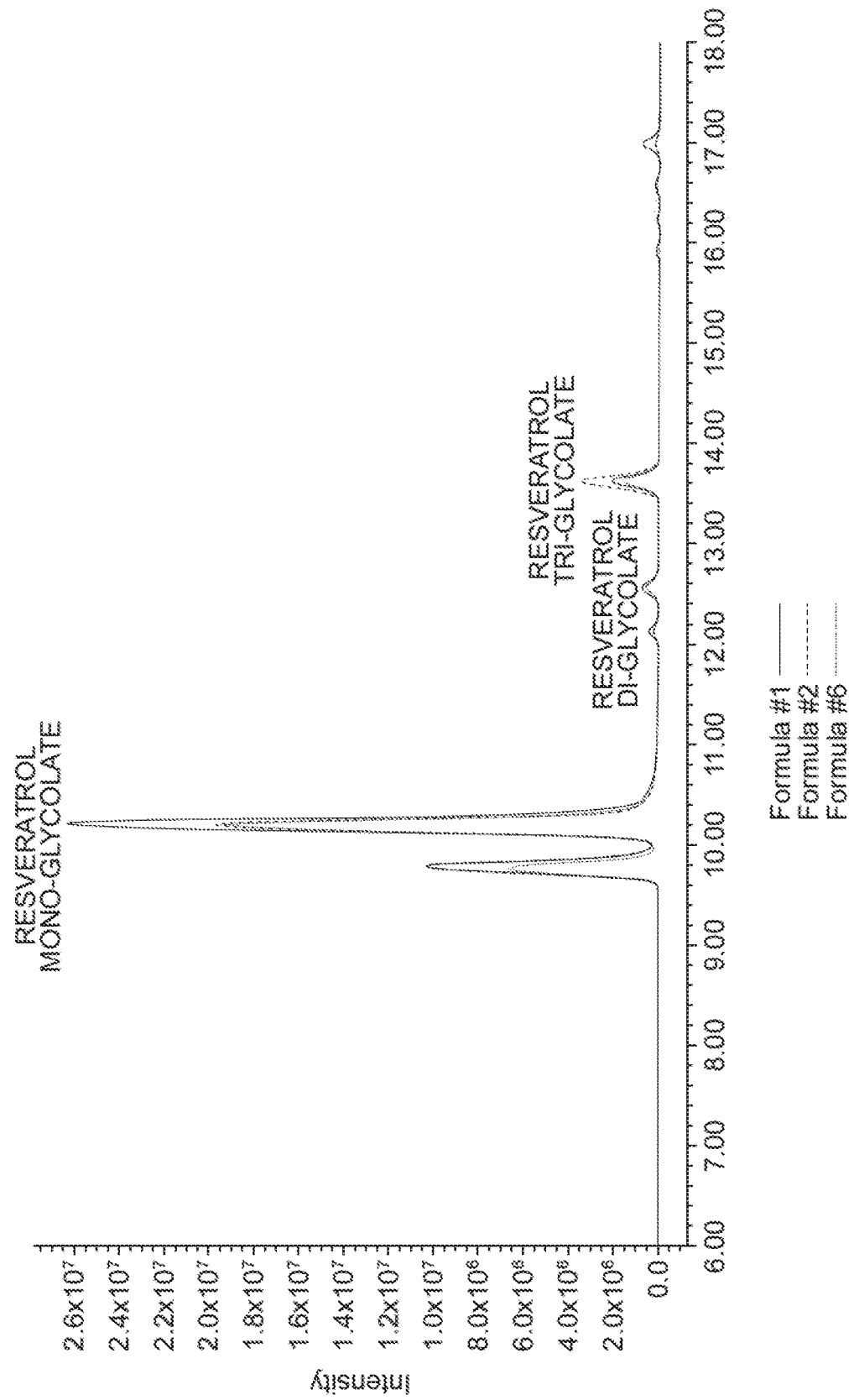
FIG. 5 shows the HPLC chromatogram of resveratrol mono glycolate (1%) at 50° C.
Figure 6:
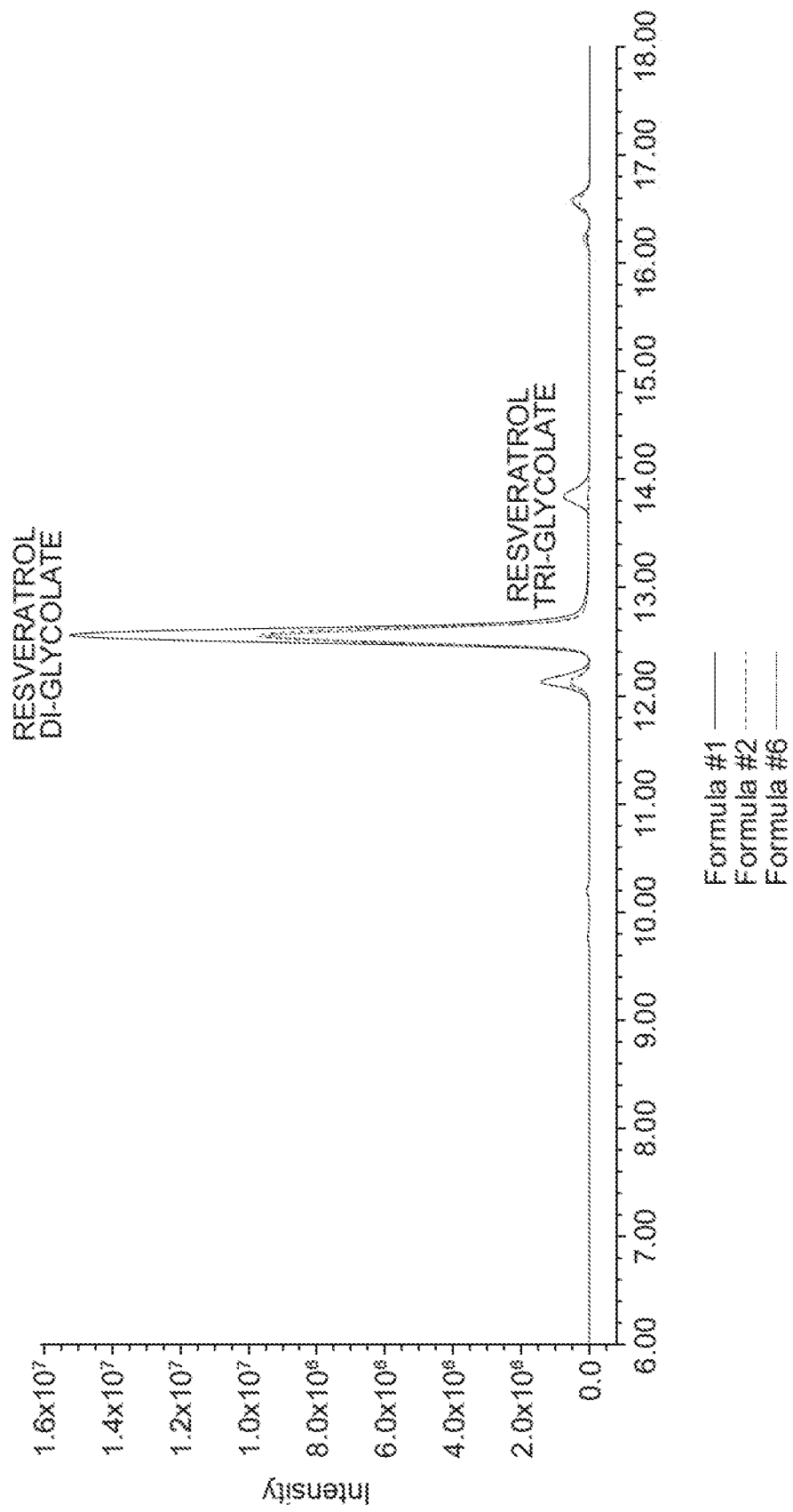
FIG. 6 shows the HPLC chromatogram of resveratrol di glycolate (1%) at 50° C.

FIG. 4 shows the HPLC chromatogram of resveratrol glycolate (1%) at 50° C. FIG. 5 shows the HPLC chromatogram of resveratrol mono glycolate (1%) at 50° C. FIG. 6 shows the HPLC chromatogram of resveratrol di glycolate (1%) at 50° C.

Figure 7:
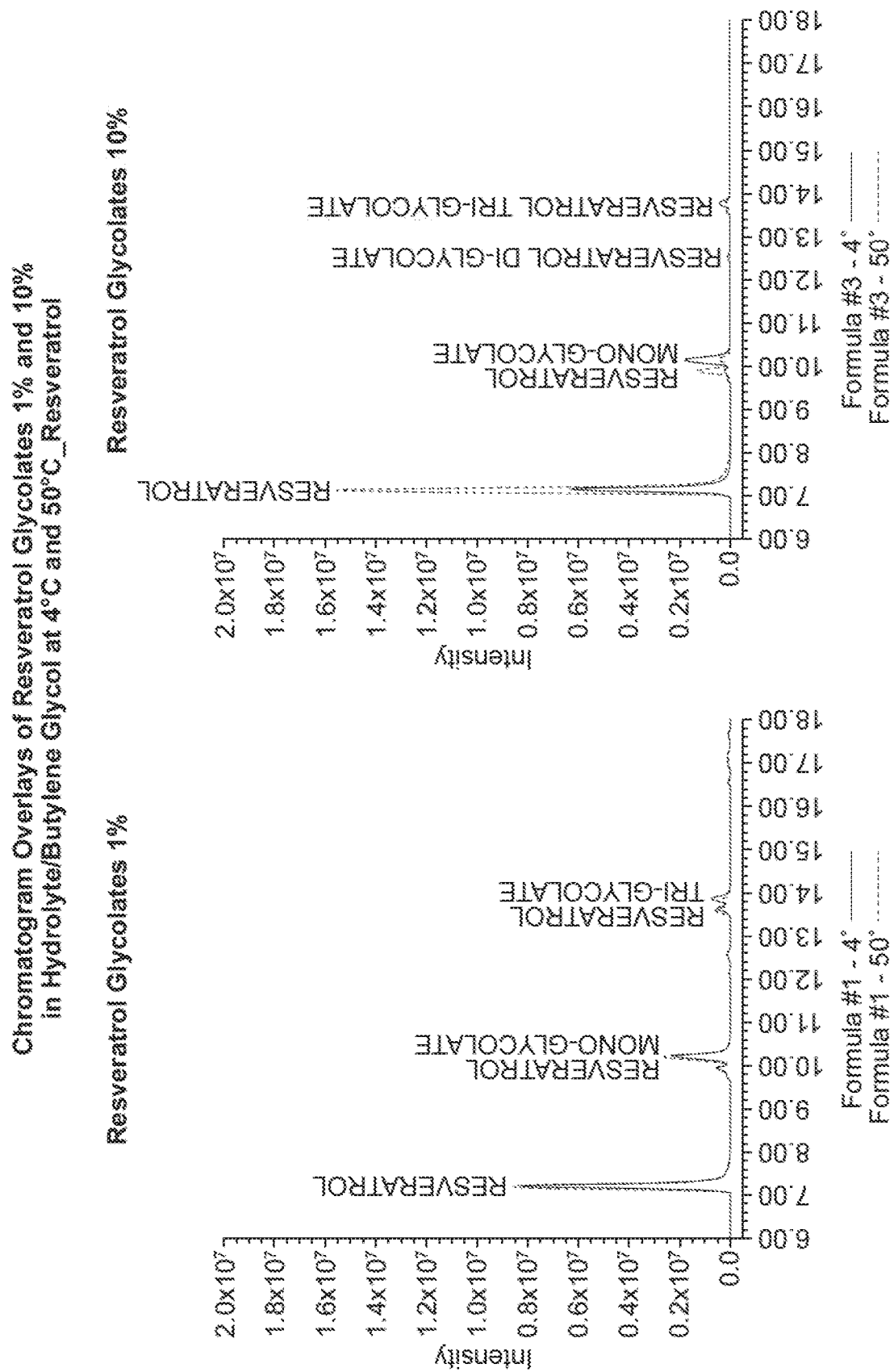
FIG. 7 shows the HPLC chromatogram of resveratrol glycolate in pentylene glycol and butylene glycol at 4° C. and 50° C., respectively.

FIG. 7 shows the HPLC chromatogram of resveratrol glycolate (1%, formula #1 and 10%, formula #3, respectively) in pentylene glycol and butylene glycol at 4° C. and 50° C., respectively. FIG. 8 shows the HPLC chromatogram of resveratrol mono glycolate (1, formula #1 and 10%, formula #3, respectively) in pentylene glycol and butylene glycol at 4° C. and 50° C., respectively. FIG. 9 shows the HPLC chromatogram of resveratrol di glycolate (1%, formula #1 and 10%, formula #3, respectively) in pentylene glycol and butylene glycol at 4° C. and 50° C., respectively.

FIG. 10 shows stability of resveratrol glycolate (1%) in solution in respective formulas at 4° C. and 50° C. FIG. 11 shows stability of resveratrol mono and di glycolate (10%) in solution in respective formulas at 4° C. and 50° C. FIG. 12 shows stability of resveratrol mono and diglycolate (20%) in solution in respective formulas at 4° C. and 50° C.

Experimental results show that the combination of pentylene glycol/butylene glycol cosolvents is more stable compared to propanediol/butylene glycol or isoprene glycol cosolvents. Further, it was also observed that 10% resveratrol glycolate and 20% resveratrol glycolate solution (shown in FIGS. 11-12) exhibited higher degradation compared to 1% resveratrol glycolate solution at elevated storage conditions.

As shown in FIG. 10, Formula 1 is about 21% more stable when compared to formula 2 and formula 1 is about 23% more stable than formula 6, at 4° C. Similarly, Formula 1 is about 24% more stable when compared to formula 6 and formula 1 is about 30% more stable than formula 6, at 50° C.

As shown in FIG. 11, Formula 3 at 4° C. is about 55% more stable than at 50° C. and formula 7 at 4° C. is about 21% more stable than at 50° C.

As shown in FIG. 12, Formula 4 is about 48% more stable at 4° C. than at 50° C.

Example 9

Compositions containing the resveratrol glycolate in anhydrous formulation by weight:

| Ingredients | 1% res-gly solution (1:10:89) | 2% res-gly solution (2:10:88) | 5% res-gly solution (5:10:8) | 10% res-gly solution (1:1:8) | 20% res-gly solution (1:1:3) | 30% res-gly solution (3:3:4) |
|---|---|---|---|---|---|---|
| Resveratrol glycolate | 0.2 | 0.2 | 0.2 | 0.2 | 0.5 | 1.0 |
| Butylene glycol | 17.8 | 8.8 | 3.4 | 1.6 | 1.5 | 1.3 |
| Pentylene glycol | 2 | 1 | 0.4 | 0.2 | 0.5 | 1.0 |
| Polysilicone-11/dimethicone | 20 | 25 | 25 | 25 | 25 | 25 |
| Shea butter | 1 | 1 | 1 | 1 | 1 | 1 |
| PEG-10 Dimethicone | 1.2 | 1.2 | 1.2 | 1.2 | 1.2 | 1.2 |
| Methyltrimethicone | 16 | 16 | 16 | 16 | 16 | 16 |
| Dimethicone | 10 | 10 | 10 | 10 | 10 | 10 |
| Silica | 2 | 2 | 2 | 2 | 2 | 2 |

The composition is prepared by combining the ingredients and mixing well to form an anhydrous formulation. The ratio of resveratrol glycolate, butylene glycol and pentylene glycol is shown in respective columns, which are combined initially in a solution and then introduced into the phase of the formulation.

Example 10

Compositions containing the resveratrol glycolate in serum/gel formulation by weight:

| Ingredients | 1% res-gly solution (1:10:89) | 2% res-gly solution (2:10:88) | 5% res-gly solution (5:10:8) | 10% res-gly solution (1:1:8) | 20% res-gly solution (1:1:3) | 30% res-gly solution (3:3:4) |
|---|---|---|---|---|---|---|
| Resveratrol glycolate | 0.2 | 0.2 | 0.2 | 0.2 | 0.5 | 1.0 |
| Butylene glycol | 17.8 | 8.8 | 3.4 | 1.6 | 1.5 | 1.3 |
| Pentylene glycol | 2 | 1 | 0.4 | 0.2 | 0.5 | 1.0 |
| Caffeine | 0.2 | 0.2 | 0.2 | 0.2 | 0.2 | 0.2 |
| Disodium EDTA | 0.05 | 0.05 | 0.05 | 0.05 | 0.05 | 0.05 |
| Hydroxyethyl acrylate/sodium acryloldimethyl taurate copolymer | 0.85 | 0.85 | 0.85 | 0.85 | 0.85 | 0.85 |
| Phenoxyethanol | 0.65 | 0.65 | 0.65 | 0.65 | 0.65 | 0.65 |
| Ethyl hexyl glycerin | 0.3 | 0.3 | 0.3 | 0.3 | 0.3 | 0.3 |
| Polysorbate-60 | 0.05 | 0.05 | 0.05 | 0.05 | 0.05 | 0.05 |
| Sorbital isosterate | 0.05 | 0.05 | 0.05 | 0.05 | 0.05 | 0.05 |
| Sodium Hyaluronate | 0.05 | 0.05 | 0.05 | 0.05 | 0.05 | 0.05 |
| Water | QS | QS | QS | QS | QS | QS |

The composition is prepared by combining the ingredients and mixing well to form the formulation for serum/gel. The ratio of resveratrol glycolate, butylene glycol and pentylene glycol is shown in respective columns, which are combined initially in a solution and then introduced into the phase of the formulation.

Example 11

Compositions containing the resveratrol glycolate in cream/lotion formulation by weight:

| Ingredients | 1% res-gly solution (1:10:89) | 2% res-gly solution (2:10:88) | 5% res-gly solution (5:10:8) | 10% res-gly solution (1:1:8) | 20% res-gly solution (1:1:3) | 30% res-gly solution (3:3:4) |
| --- | --- | --- | --- | --- | --- | --- |
| Resveratrol glycolate | 0.2 | 0.2 | 0.2 | 0.2 | 0.5 | 1.0 |
| Butylene glycol | 17.8 | 8.8 | 3.4 | 1.6 | 1.5 | 1.3 |
| Pentylene glycol | 2 | 1 | 0.4 | 0.2 | 0.5 | 1 |
| Dicaprylyl carbonate | 3 | 3 | 3 | 3 | 3 | 3 |
| Isononyl isononanoate | 2.25 | 2.25 | 2.25 | 2.25 | 2.25 | 2.25 |
| Steareth-2 | 2.1 | 2 | 2.1 | 2.1 | 2.1 | 2.1 |
| Di-C12-15aklyl fumarate | 2 | 2 | 2 | 2 | 2 | 2 |
| Glycerin | 2 | 2 | 2 | 2 | 2 | 2 |
| Steareth-21 | 1.4 | 1.4 | 1.4 | 1.4 | 1.4 | 1.4 |
| Cetyl alcholol | 0.75 | 0.75 | 0.75 | 0.75 | 0.75 | 0.75 |
| Ethylhexylglycerin | 0.5 | 0.5 | 0.5 | 0.5 | 0.5 | 0.5 |
| Phenoxyethanol | 0.46 | 0.46 | 0.46 | 0.46 | 0.46 | 0.46 |
| Acrylate/C10-30 acryl crosspolymer | 0.4 | 0.4 | 0.4 | 0.4 | 0.4 | 0.4 |
| Disodium EDTA | 0.2 | 0.2 | 0.2 | 0.2 | 0.2 | 0.2 |
| Tromethamine | 0.4 | 0.4 | 0.4 | 0.4 | 0.4 | 0.4 |
| Water | QS | QS | QS | QS | QS | QS |

The composition is prepared by combining the ingredients and mixing well to form the formulation for cream/lotion. The ratio of resveratrol glycolate, butylene glycol and pentylene glycol is shown in respective columns, which are combined initially in a solution and then introduced into the phase of the formulation.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:

1. A process for solubilizing a resveratrol glycolate compound, comprising the steps of:
    (a) initially heating the resveratrol glycolate compound, and
    (b) mixing the heated resveratrol glycolate compound with at least one glycol solvent at room temperature for ten minutes to one hundred and twenty minutes, wherein the at least one glycol solvent comprises pentylene glycol and butylene glycol in a ratio from 1:1 to 1:50.

2. The process according to claim 1, wherein the resveratrol glycolate is present from 0.1% to 30% by weight of the solution.

3. The process according to claim 2, wherein the at least one glycol solvent further comprises propanediol, phenoxyethanol, butylene glycol, pentylene glycol, isoprene glycol, propylene glycol caprylate, ethoxydiglycol, butoxydiglycol glycerin and combinations thereof.

4. The process according to claim 1, wherein the heating step is performed at a temperature not greater than 45° C.

5. The process according to claim 3, wherein the at least one glycol solvent is a combination of pentylene glycol and butylene glycol.

6. The process of claim 1, wherein the resveratrol glycolate comprises the formula:

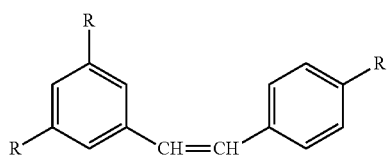

wherein each R is independently selected from:
(i) —OH, or
(ii)

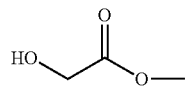

wherein all three R groups cannot simultaneously be —OH.

7. A product obtained by the process according to claim 6.

* * * * *